United States Patent [19]
Göbel

[11] Patent Number: 5,418,262
[45] Date of Patent: May 23, 1995

[54] ADHESIVE, WATERPROOF AND HYDROLYSIS-RESISTANT BONDING LAYER FOR METAL, CERAMIC, GLASS, POLYMER-PLASTIC BONDS AND DISPERSION FOR PRODUCING IT

[75] Inventor: Roland Göbel, Jena, Germany

[73] Assignee: Heraeus Kulzer GmbH, Hanau, Germany

[21] Appl. No.: 98,376

[22] PCT Filed: Dec. 5, 1992

[86] PCT No.: PCT/EP92/02820

§ 371 Date: Aug. 9, 1993

§ 102(e) Date: Aug. 20, 1993

[87] PCT Pub. No.: WO93/11732

PCT Pub. Date: Jun. 24, 1993

[30] Foreign Application Priority Data

Dec. 9, 1991 [DE] Germany .................. 41 40 504.8
Aug. 27, 1992 [DE] Germany .................. 42 28 530.5

[51] Int. Cl.$^6$ .................. A61K 6/08; C08L 61/04
[52] U.S. Cl. .................. 523/116; 523/118; 523/120; 524/595; 524/596; 525/132; 525/502; 433/228.1
[58] Field of Search ........... 523/115, 116, 118, 120; 524/594, 595, 596, 611; 526/313, 279, 315, 321; 433/226, 228.1; 427/407.1; 428/447, 500, 506; 525/132, 502

[56] References Cited

U.S. PATENT DOCUMENTS

| | | | |
|---|---|---|---|
| 3,011,909 | 12/1961 | Hart et al. | 428/506 |
| 4,364,731 | 12/1982 | Norling | 433/218 |
| 4,407,984 | 10/1983 | Ratcliffe et al. | 523/118 |
| 4,600,390 | 7/1986 | Gobel | 433/218 |
| 5,049,190 | 9/1991 | Göbel | 106/35 |
| 5,069,956 | 12/1991 | Murata et al. | 523/412 |

FOREIGN PATENT DOCUMENTS

| | | |
|---|---|---|
| 0223067 | 5/1987 | European Pat. Off. . |
| 2227309 | 11/1974 | France . |
| 2420771 | 9/1976 | Germany . |
| 3332179 | 6/1984 | Germany . |
| 3802043C1 | 7/1989 | Germany . |
| 276453A1 | 2/1990 | Germany . |
| 0006791 | 1/1977 | Japan . |
| 1459841 | 12/1976 | United Kingdom . |
| 1459843 | 12/1976 | United Kingdom . |
| 279018 | 2/1974 | U.S.S.R. . |

OTHER PUBLICATIONS

List per MPEP 608.01(v) of dental alloys and dental resin materials identified in specification by respective trademarks.
Heraeus Edelmetalle GmbH brochure about High Gold Content Casting Alloys pp. 7–9.
Degusssa AG brochure about "Degulor M" pp. 4–11.
Wieland Edelmetalle GmbH & Co. brochure about Auropal 2 (Aug. '93).
Wieland Edelmetalle GmbH & Co. brochures about Duo Pal 6 and Simidur S2 (Aug. '93)
Heraeus Kulzer GmbH brochure about Estilux pp. 5–20 (Jul. '86).
Heraeus Kulzer GmbH brochure about Charisma (Apr. '93).
Heraeus Kulzer GmbH brochure about Palavit 55.
Kulzer & Co. GmbH brochure about Dentacolor pp. 1–2 (Apr. '74).
Kulzer & Co. GmbH brochure about Dentacolor pp. 1–6 (Nov. '84).

Primary Examiner—Paul R. Michl
Assistant Examiner—Tae H. Yoon
Attorney, Agent, or Firm—Frishauf, Holtz, Goodman & Woodward

[57] ABSTRACT

A dispersion for producing an adhesive, waterproof and hydrolysis-resistant bonding layer for bonding metal, ceramics, glass and for polymer-plastic bonds, including a phenol resin-methacrylate dispersion containing phenol with free methylol groups, one or more mono- or multifunctional methacrylate compounds, dispersed acrylate, water and acetone.

15 Claims, No Drawings

ADHESIVE, WATERPROOF AND HYDROLYSIS-RESISTANT BONDING LAYER FOR METAL, CERAMIC, GLASS, POLYMER-PLASTIC BONDS AND DISPERSION FOR PRODUCING IT

The invention relates to an adhesive, waterproof hydrolysis-resistant bonding layer for metal, ceramic, glass, and polymer-plastic bonds and a dispersion for producing it. The bonding layer of the invention is preferably used for bonds which are exposed to steady mechanical and temperature-change stresses, along with simultaneous moisture action, in this case for bonds in dental technology in particular.

Numerous suggestions for bonding plastics with metal surfaces in a gapless manner have been made in the past years. The basic principle of these processes is that in a first step an inorganic (mostly silicate) layer is applied to a metal surface (silicate treatment) and that in a second step the surface is coated with a functional alkoxysilane (silane treatment). In this case the adhesive silane (mostly hydrolized γ-methacryloyloxypropyl-trimethoxysilane) constitutes the bond between the inorganic silicate layer and a methacrylate-containing plastic dental material, wherein on the one hand the free OH groups of the adhesive silane, with the surface OH groups of the silicate layer, are chemically bonded to the silicate layer in the course of condensation reactions while, on the other hand, there is bonding to a plastic dental material for example, via the methacrylate group of the adhesive silane. The known processes are distinguished by the methods of the different application of the silicate layer, while the application of the adhesive silane is almost identical in all described processes.

U.S. Pat. No. 4,364,731 describes a process for applying a silicon dioxide layer to metallic denture parts for a high-frequency magnetron sputtering device. Since a vacuum coating installation is required for this, the process requires a considerable outlay for apparatus.

In DE-PS 34 03 894 the application of the silicate layer takes place by means of a clearly more simple flame-hydrolysis process of the tetraethoxysilane whereby, however, good adhesion of the plastic to the metal is only attained when the apparatus parameters are strictly adhered to.

Furthermore, a process is described in DD 276 453 in which a silicate-chromium oxide layer is applied to a dental alloy surface by means of a sol-gel solution and is fixed by means of a subsequent tempering process (320° C., 2 to 8 min). Dental alloys with an increased copper content (>5% of mass) in particular reveal themselves as being critical, because in this case copper(II)-oxide, which does not adhere well to the alloy surface, is formed by the tempering process, because of which the metal-plastic bond is weakened.

A method is described in DE-PS 38 02 043 in which the silicate layer is applied in a sand-blasting process by adding a defined amount of silicon dioxide of a mean particle size $\leq 5$ μm to the abrasive corundum. In the course of this, local energy densities appear in the impact area of the corundum particles, which are sufficient to fuse the fine silicate particles to the metallic surface. With this process, too, sufficient bonding adhesion can only be achieved with the most scrupulous adherence to the operating parameters.

The known described processes all require an expensive outlay in apparatus or chemicals and several process steps. In addition, when used in the dental field, the Si-O-Si bonds of the silicate layer are subjected to continuous hydrolysis attack because of the constant exposure of the plastic-metal bonds to moisture in the mouth area, which can result in a weakening of the bond adhesion during prolonged exposure.

Thus it is the object of the invention to recite an adhesive, waterproof and hydrolysis-resistant layer which can be produced with little outlay in apparatus and which is suitable for bonding plastics, in particular methacrylate-containing plastic dental materials or adhesives, in a durable manner with a high degree of adhesiveness and free of edge gaps to metal, glass, ceramic or organic surfaces.

The object of the invention is attained by the means recited in the characterizing parts of the claims.

A dispersion is used for making the bonding layer which in accordance with the invention consists of a phenol-formaldehyde dispersion (in addition to phenol as the initial monomer, it is of course also possible to use phenol derivatives, such as cresylol and resorcinol as reaction partners) with hydroxymethylated phenol with free methylol groups, polyvinyl formal or polyvinyl butyral as plasticizing component, dispersed acrylate, distilled water and acetone. One or several mono- or multifunctional methacrylate compounds such as urethane methacrylates and hydroxy methacrylates are added to this dispersion. These polymerizable, olefinically unsaturated monomers can also be alkoxysilanes with at least one polymerizable olefinically unsaturated group, such as 3-glycidoxypropyltriethoxy silane, aminothylaminopropyltrimethoxy silane, methacrylic acid-3-trimethoxysilylpropyl ester or vinyltrimethoxysilane. The alkoxysilane can have one, two or three methoxy or ethoxy groups and one functional organic group. In particular, a phenol resin dispersion to be used for the invention contains, in relation to 100 ml dispersion, 0.5 to 5 g phenol resin and phenol with free methylol groups, 0.05 to 0.5 g of polyvinyl formal or polyvinyl butyral, 1 to 5 g dispersed acrylate, 10 to 30 ml distilled water and 10 to 30 ml acetone, wherein the amount of phenol with free methylol groups is 0.05 to 0.2% of the mass in relation to the dispersion. 2 to 20 g of one or several mono- or multifunctional methacrylate compounds are added to this dispersion, so that the result is a phenol resin-methacrylate dispersion of the invention. This dispersion is applied to a metal, glass, ceramic or organic surface and subjected to a heat treatment at between 120° to 220° C. In the course of this the methylolphenols condense via the A-stage and B-stage resins finally through spatially cross-linked C-stage resins to form the bonding layer of the invention. The methacrylate monomers can be linked by means of base-catalytic addition reactions of the methylene group of the methacryl monomer to the carbonyl function of the aldehyde (aldol addition) or bonded by interpenetrating linkages to this phenol resin space network. The dispersion has a pH of 7.2 to 8.

The attainment of the object of the invention has the following advantages over the state of the art:
- The applied coating prevents the diffusion of water which weakens the bonding of a plastic or an adhesive to a surface of a metal alloy, for example.
- The solidification of the coating takes place in a relatively low temperature range (120° to 220° C.), so that there are no discolorations or scale formations, for example on critical dental alloys.

The attainment of the object of the invention is completely independent of the bonding materials which are to be brought into contact.

No additional adhesive agent is required with the attainment of the object of the invention, because the molecules of the adhesive agent have already been integrated in the bonding layer.

The attainment of the object of the invention can be realized with little outlay for apparatus, such as simple heat sources, and without problems in any area of use without the necessity of expensive adherence to process parameters.

Advantageous embodiments of the invention, particularly its use in dental technology, ensue from the dependent claims and will be described in detail in the following exemplary embodiments which do not limit the invention.

The subsequently cited tension or pressure shear strength values of metal-plastic bonds or metal-metal adhesions are used to demonstrate the attainment of the object of the invention without being in a position to describe the type of the adhesion mechanism which occurs, because in this case explanations of the adhesions used up to now need to be revised.

The unconditioned surface is used as a comparison value (blank value) of the bonding strength, wherein this surface as well as the surfaces used for the invention are first sand-blasted (aluminum corundum 50 to 250 μm, 1 to 5 bar). A further comparison value is the adhesive strength which is achieved if the surfaces of the solid bodies are coated with only a portion of the dispersion in accordance with the invention (Dispersion A), and finally as the third comparison value the shear strength which can be achieved with the dispersion of the invention.

Composition of the Dispersion A:

0.75 g phenol resin and phenol with free methylol groups
0.1 g polyvinyl formal or polyvinyl butyral
2 g dispersed acrylate
20 ml distilled water
60 ml isopropanol
20 ml acetone To obtain the composition of the invention (Dispersion B), the following was added to 100 ml of this dispersion, the content of phenol with free methylol groups of which is 0.1% of mass:

2 g methacrylic acid-3-trimethoxysilylpropyl ester
5 g methylmethacrylate
2 g triethyleneglycoldimethacrylate
1 g 2,4-butandioldimethacrylate
1 g trimethylolpropanetriacrylate
0.1 g camphor quinone
0.2 g triethanolamine In the example, this dispersion as well as the dispersion A for providing the said comparison values by itself, are applied to sand-blasted dental alloys and are subjected to a heat treatment at 120° to 220° C., preferably 150° C., for approximately 15 minutes. It is furthermore possible to apply to this surface a light-hardening opaqueing agent on a methacrylate basis and to polymerize it. Following this, a cylinder (in the example with a diameter of 5 mm and height of 2 mm) of light-hardening plastic is formed and also polymerized. In this case it is advantageous to add to the dispersion of the invention 0.1 to 1% by mass of photo-active components, such as the system of camphor quinone and triethanolamine or N,N-dimethylaminoethylmethacrylate or the like, which results in further adhesion improvement. The metal-plastic bonds made in this way are boiled for one hour in distilled water, are stored in water for 24 h and are subsequently tested for bonding strength in a pressure shear test (feed speed 1 mm min$^{-1}$). The bonding strength values obtained are shown in Tables 1 and 2.

TABLE 1

Metal-Plastic Bond (Plastic: Dentacolor)

| Dental Alloy | Shear Strength Blank value | Shear Strength Dispersion A | Shear Strength Dispersion B |
|---|---|---|---|
| Maingold | 11 MPa | 12 MPa | 16 Mpa |
| Degulor | 10.5 MPa | 11 MPa | 15.5 MPa |
| Palliag | 9 MPa | 11 MPa | 18 MPa |
| Auropal 2 | 10.8 MPa | 11.2 MPa | 16.5 MPa |
| Duo Pal 6 | 8.8 MPa | 10.4 MPa | 16.5 MPa |
| Simidur | 7.9 MPa | 10.2 MPa | 16.9 MPa |
| Wiron 88 | 7.2 MPa | 9.5 MPa | 15.3 MPa |

"DENTACOLOR" has the following physical properties:

| Physical properties | Average values |
|---|---|
| Compressive strength | 392 MPa |
| | 55740 psi |
| Flexural strength DIN 13922 | 68 N/mm$^2$ |
| | 68 MPa |
| | 9667 psi |
| Vickers hardness (HV 0.3) after 24 hours in water of 37° C. | 350 N/mm$^2$ 56880 psi |
| Water absorption | 0.7% by weight |
| Color stability test (UV-light/heat) DIN 13922 | Complies with standard |
| Total filler content | approx. 72.0% by weight |
| Inorganic filler content | approx. 51.0% by weight |

TABLE 2

Metal-Plastic Bond (Metal: Wiron 88)

| Dental Alloy | Shear Strength Blank value | Shear Strength Dispersion A | Shear Strength Dispersion B |
|---|---|---|---|
| P 50 | 15.4 MPa | 16.7 MPa | 28.5 MPa |
| Estilux | 15.1 MPa | 16.8 MPa | 26.8 MPa |
| Visio-Molar | 13.4 MPa | 15.2 MPa | 25.6 MPa |
| Charisma | 12.1 MPa | 14.8 MPa | 23.2 MPa |
| Heliomolar | 11.2 MPa | 12.5 MPa | 19.5 MPa |

"WIRON 88" has the following composition based on mass %: 64% Ni, 24% Cr, 10.0% Mo, 1.5% Si and 0.5% Ce.

In addition to the metal-plastic bonds shown in Tables 1 and 2, the tension shear strength values shown in Table 3 are used to further prove the success of the invention. Conditioning of the metal surface took place analogously to the process already described in connection with the production of the metal-plastic bonds. The length of overlap of the glued spot in this case is 10 mm and the glued area 50 mm$^2$. These glued pieces were boiled for 10 hours.

TABLE 3

Metal-Metal Adhesion (Metal: Wiron 88)

| Adhesive | Shear Strength Blank value | Shear Strength Dispersion A | Shear Strength Dispersion B |
|---|---|---|---|
| Chemiace | 12.8 MPa | 14.5 MPa | 28.5 MPa |
| Brilliant Enamel Kit | 14.4 MPa | 16.3 MPa | 25.2 MPa |
| Palavit 55 | 12.1 MPa | 13.8 MPa | 25.4 MPa |
| Microfill pontic | 11.2 MPa | 13.2 MPa | 20.8 MPa |
| Helapox blue | 9.5 MPa | 20.2 MPa | 19.5 MPa |

In a comparison between the methacrylate-containing dental adhesives Chemiace, Brilliant enamel kit, Palavit 55 and Microfill pontic, Helapox blue (epoxy resin) takes up a certain special position.

The tension shear strength of the metal-metal adhesions as well as the pressure shear strength of the metal-dental plastic bonds show that with the solution in accordance with the invention an approximately 100% higher adhesive strength can be attained in comparison to unconditioned surfaces. The break is a pure cohesion break. An adhesive, water-proof and hydrolysis-resistant bonding layer is available by means of the invention which is suitable for the most diverse bonds and is therefore not limited to application in dental technology. A use of the dispersion of the invention, which is also advantageous as a lacquer base coat, is provided in machine and autobody construction, by means of which a clear increase in the life of the bonding layer system can be achieved even under tropical conditions.

I claim:

1. A dispersion for producing an adhesive, water-proof and hydrolysis-resistant bonding layer for bonding metal, ceramics, glass and for polymer-plastic bonds, comprising a dispersed phenol resin containing phenol with free methylol groups, one or more mono- or multifunctional methacrylate compounds, dispersed acrylate, distilled water and acetone.

2. The dispersion in accordance with claim 1, which comprises 100 ml of a phenol resin dispersion, which contains 0.5 to 5 g phenol resin containing phenol with free methylol groups, 0.05 to 0.5 g of polyvinyl formal or polyvinyl butyral, 1 to 5 g dispersed acrylate, 10 to 30 ml distilled water and 10 to 30 ml acetone, and 2 to 20 g of one or more mono- or multifunctional methacrylate compounds.

3. The dispersion in accordance with claim 1, wherein the methacrylate compounds are selected from the group consisting of urethane methacrylates and hydroxy methacrylates.

4. The dispersion in accordance with claim 1, which further comprises an alkoxysilane.

5. The dispersion in accordance with claim 4, wherein the the alkoxysilane has three, two or one methoxy or ethoxy group and at least one functional organic group.

6. The dispersion in accordance with claim 5, wherein the functional organic group of the alkoxysilane is a vinyl, methacrylate or an epoxy group.

7. The dispersion in accordance with claim 6, wherein the alkoxysilane is selected from the group consisting of vinyltrimethoxy silane, methacrylic acid-3-trimethoxysilylpropyl ester, 3-glycidoxypropyltriethoxy silane and aminoethylaminopropyltrimethoxy silane.

8. The dispersion in accordance with claim 1, which further comprises 0.1 to 1% of mass of one or more photo-active components in relation to the mass of the methacrylate compounds.

9. The dispersion in accordance with claim 8, wherein the photo-active component is a photo-active system of camphor quinone and triethanolamine or N,N-dimethylaminoethylmethacrylate.

10. The dispersion in accordance with claim 1, wherein the dispersion has a pH value between 7.2 and 8.

11. An adhesive lacquer bonding layer for use in machine and autobody construction, produced by heat treating for hardening a lacquer base coat comprising a dispersed phenol resin containing phenol with free methylol groups, dispersed acrylate, water, acetone and one or more mono- or multifunctional methacrylate compounds.

12. A lacquered body comprising a substrate having bonded thereto an adhesive bonding layer in accordance with claim 11, wherein the lacquer base coat is hardened by a heat treatment at a temperature from 120° to 220° C., and one or more lacquer coats are attached to the resultant hardened lacquer base coat.

13. The dispersion in accordance with claim 1, wherein the phenol with free methylol groups is contained in an amount of 0.05 to 0.2% of the mass of the dispersion.

14. The dispersion in accordance with claim 2, and which further comprises 1 to 10 g of an alkoxysilane having one to three methoxy or ethoxy groups and at least one functional organic group.

15. The dispersion in accordance with claim 4, which includes the following two portions:
   (a) a phenol resin containing phenol with free methylol groups, polyvinyl formal or polyvinyl butyral, dispersed acrylate, distilled water, isopropanol and acetone; and
   (b) methacrylic acid-3-trimethoxysilylpropyl ester, methylmethacrylate, triethyleneglycoldimethacrylate, 2,4-butandioldimethacrylate, trimethylolpropanetriacrylate, camphor quinone and triethanolamine, wherein the phenol with free methylol groups being contained in an amount of 0.1% by mass of the dispersion.

* * * * *